United States Patent
Alsop, Sr.

(10) Patent No.: US 10,655,314 B2
(45) Date of Patent: May 19, 2020

(54) CHLORINE RETENTION RESERVOIR FOR A TOILET

(71) Applicant: James Richard Alsop, Sr., Charlotte, NC (US)

(72) Inventor: James Richard Alsop, Sr., Charlotte, NC (US)

(*) Notice: Subject to any disclaimer, the term of this patent is extended or adjusted under 35 U.S.C. 154(b) by 0 days.

(21) Appl. No.: 15/823,724

(22) Filed: Nov. 28, 2017

(65) Prior Publication Data

US 2018/0148914 A1 May 31, 2018

Related U.S. Application Data

(60) Provisional application No. 62/426,797, filed on Nov. 28, 2016.

(51) Int. Cl.
*E03D 9/03* (2006.01)
*A61L 2/18* (2006.01)
*E03D 9/02* (2006.01)

(52) U.S. Cl.
CPC .............. *E03D 9/038* (2013.01); *A61L 2/18* (2013.01); *A61L 2209/134* (2013.01); *E03D 2009/024* (2013.01); *E03D 2009/028* (2013.01)

(58) Field of Classification Search
CPC .................................................... E03D 9/038
USPC ........................................ 4/227.5, 222–233
See application file for complete search history.

(56) References Cited

U.S. PATENT DOCUMENTS

| | | | | |
|---|---|---|---|---|
| 2,950,959 A | * | 8/1960 | Ve Relle | B01J 4/001 422/263 |
| 4,168,550 A | * | 9/1979 | Lindauer | E03D 9/038 222/57 |
| 4,530,118 A | | 7/1985 | Richards | |
| 4,534,071 A | | 8/1985 | Russomanno | |
| 4,896,382 A | | 1/1990 | Sokol et al. | |
| 5,074,328 A | * | 12/1991 | Reinders | E03D 9/032 137/268 |
| RE33,861 E | * | 3/1992 | Zetena | B01F 1/0033 137/268 |
| 5,181,281 A | | 1/1993 | Jang | |
| 5,404,594 A | * | 4/1995 | Ring | B63B 29/14 137/268 |
| 6,625,821 B2 | | 9/2003 | Lhoste | |
| 8,719,971 B2 | * | 5/2014 | Burt | E03D 9/037 4/225.1 |

\* cited by examiner

*Primary Examiner* — Lauren A Crane
(74) *Attorney, Agent, or Firm* — Boudwin Intellectual Property

(57) ABSTRACT

The present invention provides a chlorine retention reservoir for a toilet. The chlorine retention reservoir comprises a housing having a base and a sidewall forming an interior volume with an open upper end. The open upper end includes a lip extending perpendicularly from the sidewall disposed around a perimeter thereof, wherein the lip receives a channel of a lid. The housing further includes an input port and an output port that receive a liquid therethrough. A plurality of baffles are disposed within the interior volume of the housing. A slot is disposed on an exterior surface of the housing, wherein the slot receives a fastener. The fastener removably secures the housing to an interior surface of a tank of a toilet. A chlorine tablet is placed within the housing where it is subjected to incoming water from a flush creating a chlorine solution that is discharged to a toilet bowl.

16 Claims, 6 Drawing Sheets

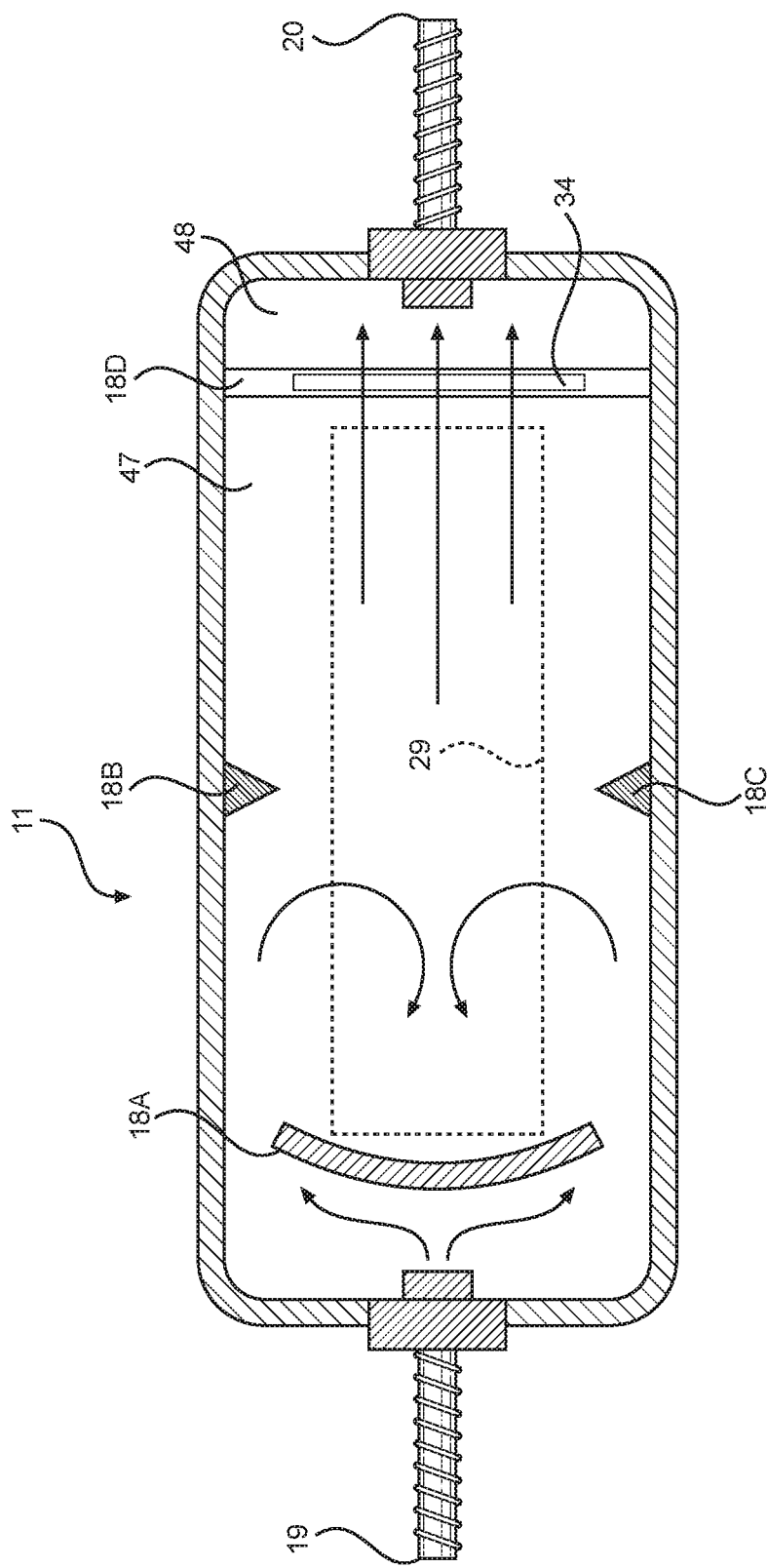

CHLORINE RETENTION RESERVOIR FOR A TOILET

CROSS REFERENCE TO RELATED APPLICATION

This application claims the benefit of U.S. Provisional Application No. 62/426,797 filed on Nov. 28, 2016. The above identified patent application is herein incorporated by reference in its entirety to provide continuity of disclosure.

BACKGROUND OF THE INVENTION

The present invention relates to cleansing fluid dispensers for toilets. More specifically, the present invention provides a chlorine retention reservoir for dispensing a concentrated chlorine solution into a bowl of a toilet immediately when the toilet is flushed. The chlorine retention reservoir is designed to hold a commercial chlorine tablet within the housing for a rapid refill and production of a saturated chlorine solution. In use, the chlorine tablet is left partially wrapped so as to minimize erosion of the tablet. A preferred method is to remove the opposite wrapper corners, thereby allowing the fluids to coarse through the wrapper so as to partially dissolve the tablet. The flush cycle of a toilet typically takes 22 seconds. During the cycle, incoming water into the reservoir creates turbulence, designed to slowly dissolve the commercial chlorine tablet within the housing, followed by a period of calm. The tablet will continue to dissolve for a short period until the saturation point is reached. Reactivation begins immediately with the next flush as the concentrated chlorine solution is dumped into the toilet bowel, at the peak of high bactericidal activity. The turbulence begins again as fresh water from another flush enters the chlorine retention reservoir from all directions to activate the absorption of the partially protected chlorine tablet. The chlorine retention reservoir maintains a sizeable quantity of a saturated chlorine solution effective against most gram negative and gram-positive strains of bacteria, including highly resistant strains of re-emerging bacteria.

Alternatively, many people add cleansing products to the holding tank of a toilet in order to deliver a disinfectant into the toilet bowl when the toilet is flushed. One such cleansing product that is commonly used is a chlorine tablet. Typically, the tablet is placed within the holding tank where it dissolves over time when subjected to water from a flush. In many instances, the chlorine tablet does not result in a highly concentrated chlorine solution because it is subjected to a large volume of water. Furthermore, the tablet may not dissolve sufficiently within the holding tank because it is not subjected to adequate mixing. Unfortunately, this weakened dose of chlorine may not effectively kill certain chlorine resistant bacteria within the toilet bowl and can have the opposite effect thereby enhancing growth of the resistant bacteria. Because the bacteria may not be adequately destroyed, the toilet bowl retains foul odors and stains caused by the bacteria. Therefore, some users may choose to add a concentrated disinfectant to the holding tank in order to kill the bacteria within the bowl. However, when adding highly concentrated disinfectants to the holding tank, this can have a negative effect on the internal components of the holding tank. Specifically, the flapper valve and any rubber or plastic fittings may suffer from degradation when subjected to concentrated disinfectants or solvents.

Devices have been disclosed in the known art that relate to cleansing fluid dispensers for toilets. These include devices that have been patented and published in patent application publications. These devices generally relate to automatic dispensing reservoirs that dispense a concentrated cleansing fluid into the holding tank of the toilet. Many of these devices are configured to attach to the inside wall or base of the tank wherein a concentrated cleansing fluid is released into the holding tank after or during each flush. Other devices attached directly to the toilet bowl in order to deliver a cleansing solution.

These known art devices have several known drawbacks. Most of these devices are design to be placed within the holding tank of the toilet. The key feature of many of these devices is that they release a cleansing solution into the water within the holding tank prior to flushing. Certain cleansing solutions, such as chlorine solutions, tend to degrade the rubberized or plastic fittings within the tank over time. Other devices only release cleansing solutions with low concentrations of chemicals that may protect these fittings from degrading, but do not kill the majority of bacteria within the toilet bowl. Finally, devices configured to attach to the toilet bowl itself tend to be small and do not provide a significant coverage amount of disinfectant to the toilet bowl. Therefore, a chlorine retention reservoir designed to attach within the holding tank of a toilet and safely deliver a concentrated chlorine solution to a toilet bowl is needed.

In light of the devices disclosed in the known art, it is submitted that the present invention substantially diverges in design elements from the known art and consequently it is clear that there is a need in the art for an improvement to existing toilet cleansing devices. In this regard the instant invention substantially fulfills these needs.

SUMMARY OF THE INVENTION

In view of the foregoing disadvantages inherent in the known types of cleansing fluid dispensers for toilets now present in the known art, the present invention provides a new chlorine retention reservoir wherein the same can be utilized for providing convenience for the user when safely dispensing a chlorine solution to disinfect a toilet bowl.

It is therefore an object of the present invention to provide a new and improved chlorine retention reservoir device that has all of the advantages of the known art and none of the disadvantages.

It is another object of the present invention to provide a chlorine retention reservoir comprising a housing having a base and a sidewall forming an interior volume having an open upper end. The open upper end includes a lip extending perpendicularly from the sidewall disposed around a perimeter of the open upper end, wherein the lip receives a channel of a lid. The housing further comprising a plurality of baffles disposed within the interior volume of the housing and an input port and an output port disposed on the sidewall of the housing. The housing includes a slot disposed on an exterior surface, wherein the slot is configured to receive a fastener. The fastener removably secures the housing to an interior surface of a toilet reservoir.

Another object of the present invention is to provide a chlorine retention reservoir wherein the plurality of baffles comprise a first baffle affixed to the base, a second baffle and a third baffle affixed to opposing sidewalls, and a fourth affixed at a rear portion of the housing. The first baffle comprises a curved shaped, the second baffle and the third baffle comprise a triangular shape, and the fourth baffle comprises a u-shaped panel with two arms extending outwardly from a planar member.

Yet another object of the present invention is to provide a chlorine retention reservoir wherein the housing is constructed of a chlorine resistant material.

Another object of the present invention is to provide a chlorine retention reservoir that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 6 shows an overhead water flow diagram within the interior housing of the chlorine retention reservoir.

DETAILED DESCRIPTION OF THE INVENTION

Figure 1:
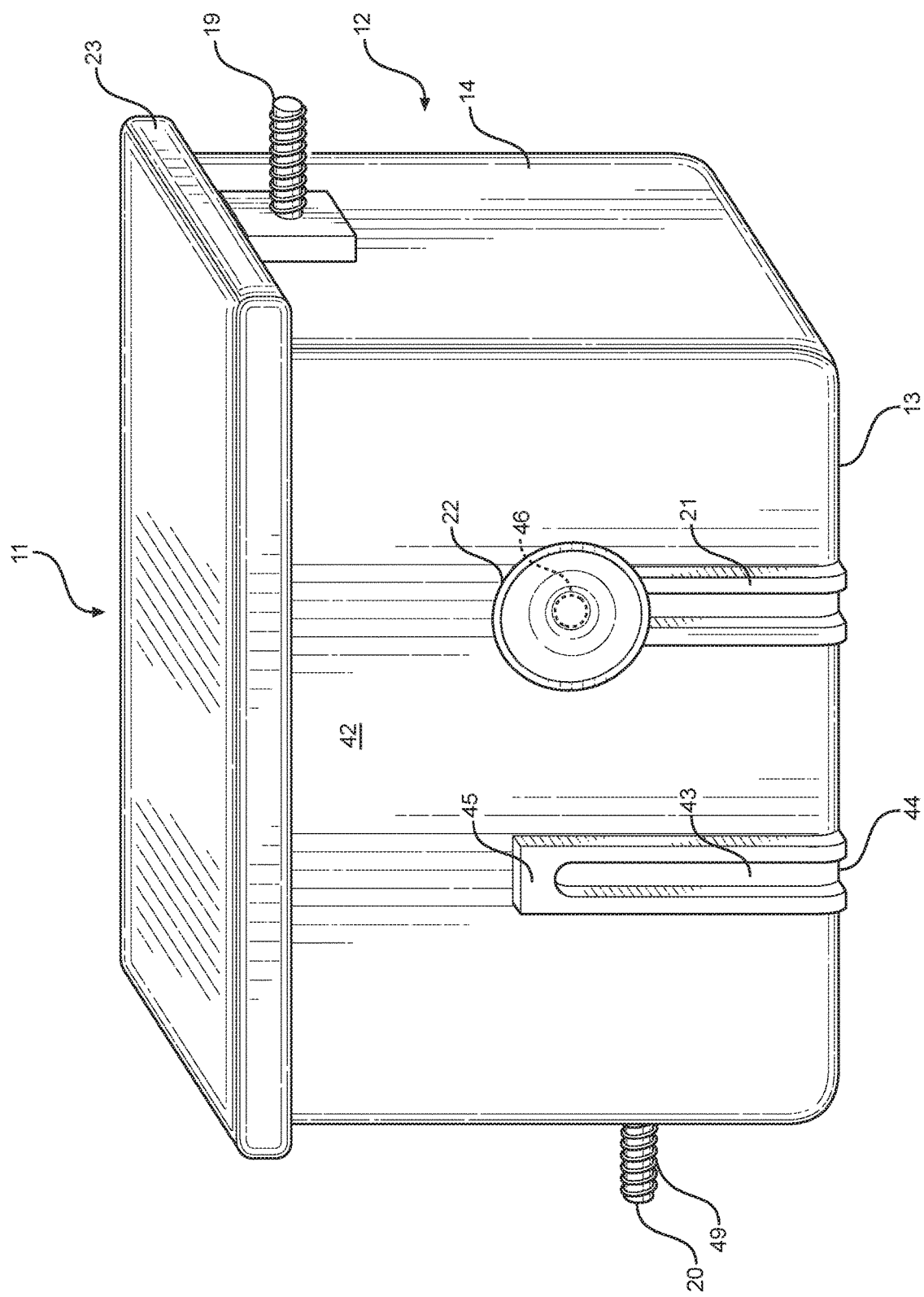
FIG. 1 shows a perspective view of an embodiment of the chlorine retention reservoir.

Reference is made herein to the attached drawings. Like reference numerals are used throughout the drawings to depict like or similar elements of the chlorine retention reservoir. For the purposes of presenting a brief and clear description of the present invention, the preferred embodiment will be discussed as used for introducing a concentrated chlorine solution into the bowl of a toilet. The figures are intended for representative purposes only and should not be considered to be limiting in any respect.

Referring now to FIG. 1, there is shown a perspective view of an embodiment of the chlorine retention reservoir. The chlorine retention reservoir 11 comprises a housing 12 having a base 13 and a sidewall 14 forming an interior volume with an open upper end, wherein the open upper end receives a lid 23 thereon. In the illustrated embodiment, the housing 12 is rectangular and sized to receive a chlorine disc. However, in alternative embodiments, the housing 12 may be any suitable shape or dimension. The reservoir 11 is constructed from a chlorine resistant material, such as polyethylene, wherein the housing 12 can withstand high chlorine concentrations without degrading. The chlorine retention reservoir 11 includes an input port 19 and an output port 20 disposed on the sidewall 14 of the housing 12. Both the input port 19 and the output port 20 are configured to receive a liquid therethrough. In the illustrated embodiment, both the input port 19 and the output port 20 comprise a threaded outer surface 49 configured to removably secure a water line of a toilet thereto. However, the ports 19, 20 may comprises any type of fastening connection, such as a quick connect coupling system.

The chlorine retention reservoir 11 further comprises a pair of slots 21 disposed on the exterior surface 42 of the housing 12. The slots 21 are configured to receive a fastener 22, wherein the fastener 22 removably secures the housing 12 to a surface of a toilet tank. In the illustrated embodiment, each slot 21 contains an elongated channel 43 having an open first end 44 and a closed second end 45. This configuration allows a protrusion 46 of a fastener 22, such as a suction cup, to slidably attach within the slot 21, wherein the protrusion 46 is fed through the open first end 44 and slides along the channel 43 where it remains secure at the closed second end 45. In the illustrated embodiment, the slot 21 extends from the base 13 of the housing 12 to half the height of the sidewall 14, wherein the height is measured from the base 13 to a lip on the open upper end. In the illustrated embodiment, the fasteners 22 are suction cups. However, in alternative embodiments, the fasteners 22 may be any type of fastener, such as a hook or an adhesive.

Figure 2:
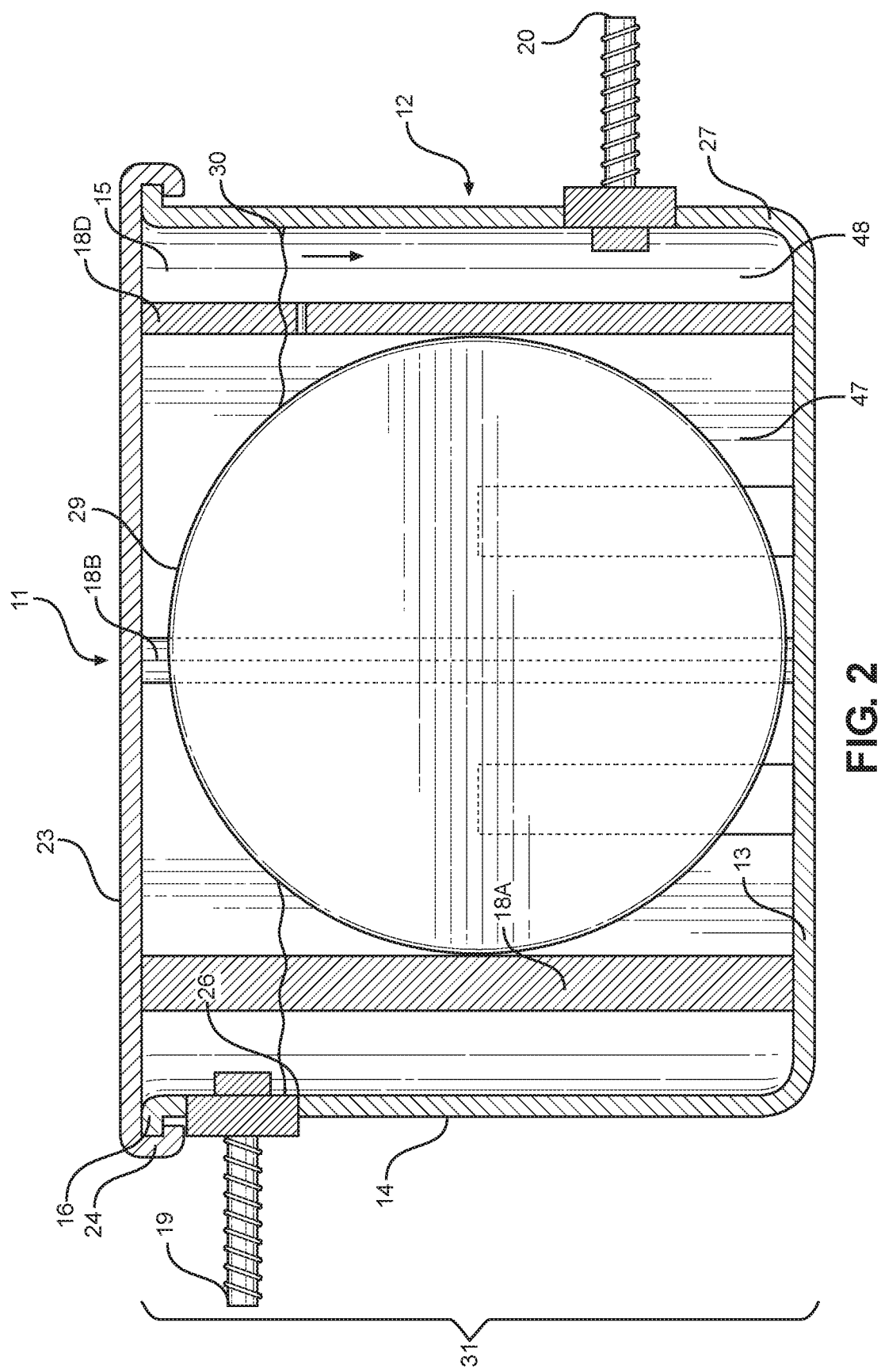
FIG. 2 shows a cross sectional view of an embodiment of the chlorine retention reservoir taken along line 2-2 of FIG. 3.
Figure 3:
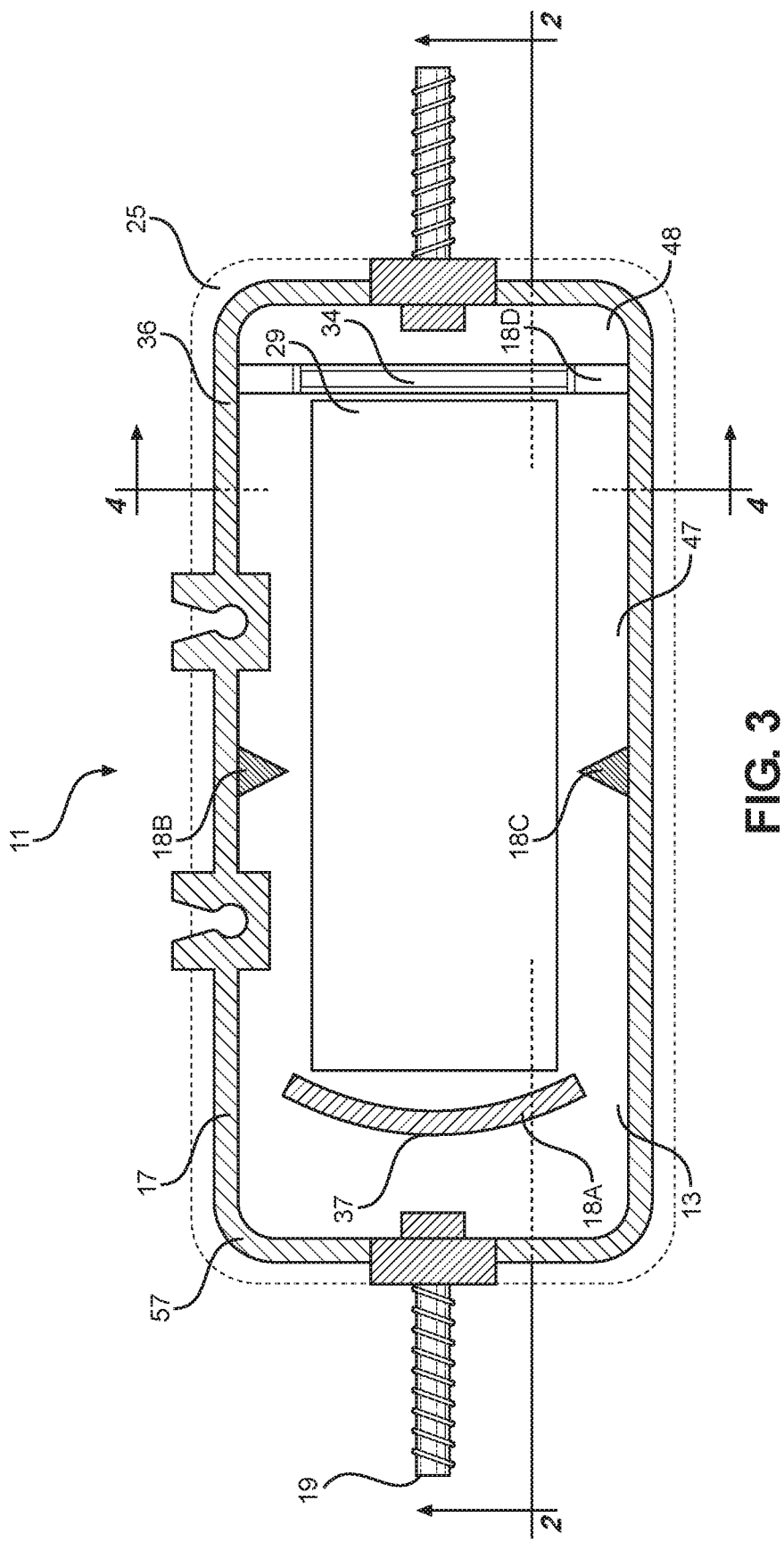
FIG. 3 shows a top view of an embodiment of the chlorine retention reservoir.

Referring now to FIGS. 2 and 3, there is shown a cross sectional view of an embodiment of the chlorine retention reservoir taken along line 2-2 of FIG. 3, and a top elevational view of an embodiment of the chlorine retention reservoir, respectively. In the illustrated embodiment, the open upper end 15 of the housing 12 includes a lip 16 extending perpendicularly from the sidewall 14. The lip 16 extends around a perimeter 17 of the open upper end 15 of the housing 12. The lid 23 of the chlorine retention reservoir 11 includes a U-shaped channel 24 disposed along a perimeter 25 of a lower surface, wherein the U-shaped channel 24 is configured to receive the lip 16 of the open upper end 15, such that the lid 23 removably secures to the lip 16. The removably securable lid 23 allows a user to access the interior of the housing 12 in order to place a dissolvable chlorine disc 29 stored therein.

In the illustrated embodiment, the input port 19 and the output port 20 are disposed on opposing sidewalls 14. The input port 19 is disposed at an upper portion 26 of the sidewall 14, while the output port 20 is disposed at a lower portion 27 of the sidewall 14. When a toilet is flushed, this configuration allows fresh water to flow through the input port 19 and into a mixing chamber 47, wherein the water is mixed with the dissolvable chlorine disc 29 stored within the housing 12. The flush cycle of a toilet typically takes twenty-two seconds. During the cycle, incoming water into the reservoir creates turbulence, designed to slowly dissolve the chlorine disc 29 disposed within the housing, which is then followed by a period of calm. The tablet will continue to dissolve for a short period until the saturation point is reached. Reactivation begins immediately with the next flush as the concentrated chlorine solution is dumped into the toilet bowel, at the peak of high bactericidal activity. The turbulence begins again as fresh water from another flush enters the chlorine retention reservoir from all directions to activate the absorption of the partially protected chlorine disc 29. The chlorine retention reservoir 11 maintains a sizeable quantity of a saturated chlorine solution effective against most gram negative and gram-positive strains of bacteria, including highly resistant strains of re-emerging bacteria. The size of the housing 12 is designed to receive a limited amount of water, such that a concentrated chlorine solution 30 is created. Once mixed, the concentrated chlorine solution 30 flows into a discharge chamber 48 wherein it is dispelled through the output port 20 of the reservoir 11. The chlorine solution 30 is deposited within the bowl of the toilet, wherein it is used to kill bacteria on the surface of the bowl. The location of the input port 19 at the upper portion 26 helps prevent the chlorine solution 30 from back flowing out of the reservoir 11, while the location of the output port 20 at the lower portion 27 aides in discharging the solution out of the reservoir 11.

The chlorine retention reservoir 11 further includes a plurality of baffles 18 A-D disposed within the interior volume of the housing 12. The baffles 18 A-D are configured to divert and mix water that is received into the reservoir 11 with the dissolvable chlorine disc 29. In the illustrated embodiment, a first baffle 18A comprising a curved shape is affixed to the base 13, wherein the first baffle 18A extends perpendicularly therefrom. The first baffle 18A extends a height 31 of the sidewall 14, wherein the height 31 is measured from the base 13 to the lip 16 at the open upper end 15 of the housing 12. The first baffle 18A comprises a curved shape, wherein an apex 37 of the curve faces the input port 19, such that when water is received through the input port 19, the water contacts the apex 37 and is dispersed throughout the interior of the housing 12. The interior of the housing 12 further includes a plurality of curved corners 57, wherein the curve of each corner aides in maintaining a constant flow of fluid within the interior of the housing 12 once the water is dispersed.

The chlorine retention reservoir 11 includes a second baffle 18B and a third baffle 18C affixed to opposing sidewalls within the interior volume of the housing 12. Both the second baffle 18B and third baffle 18C comprise a triangular shape that extends the height 31 of the sidewall 14. The second baffle 18B and third baffle 18C protrude outwardly from the respective sidewall 14 in order to create turbulence within the chlorine solution 30 when subjected to a flow of liquid. In this way, the baffles 18B, 18C assist in the mixing of water with the dissolvable chlorine disc 29 to create the chlorine solution 30. A fourth baffle 18D is disposed at a rear end 36 of the housing 12 such the fourth baffle 18D separates the interior volume of the housing 12 into the mixing chamber 47 and the discharge chamber 48. The mixing chamber 47 is configured to secure the dissolvable chlorine disc 29 and receive water therein, while the discharge chamber 48 receives the chlorine solution 30 that overflows through a channel 34 of the fourth baffle 18D.

Figure 4:
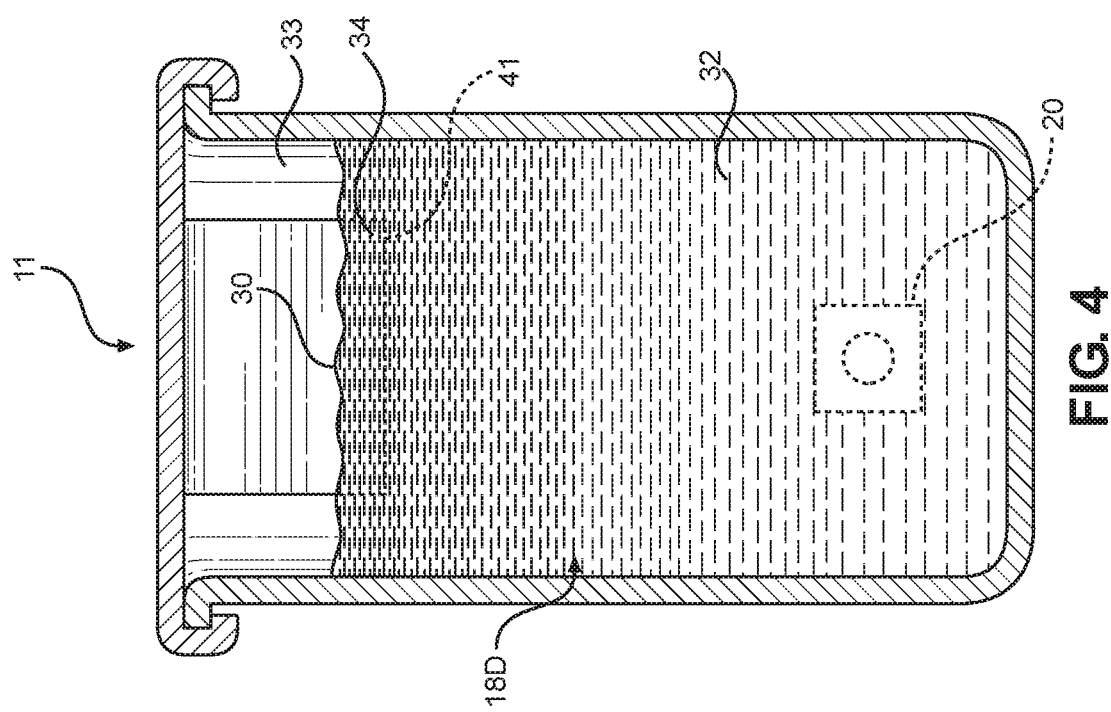
FIG. 4 shows a cross sectional view of an embodiment of the fourth baffle of the chlorine retention reservoir taken along line 4-4 of FIG. 3.

Referring now to FIG. 4, there is a cross sectional view of an embodiment of the fourth baffle of the chlorine retention reservoir taken along line 4-4 of FIG. 3. The fourth baffle 18D comprises a planar member 32 having a pair of arms 33 extending therefrom, wherein a channel 34 is disposed between the pair of arms 33. The channel 34 is configured to allow the chlorine solution 30 to pass over an edge 41 of the planar member 32. Once the chlorine solution 30 passes over the edge 41, it is deposited within the discharge chamber, wherein it exits through the output port 20 of the housing and into the toilet bowl.

Figure 5:
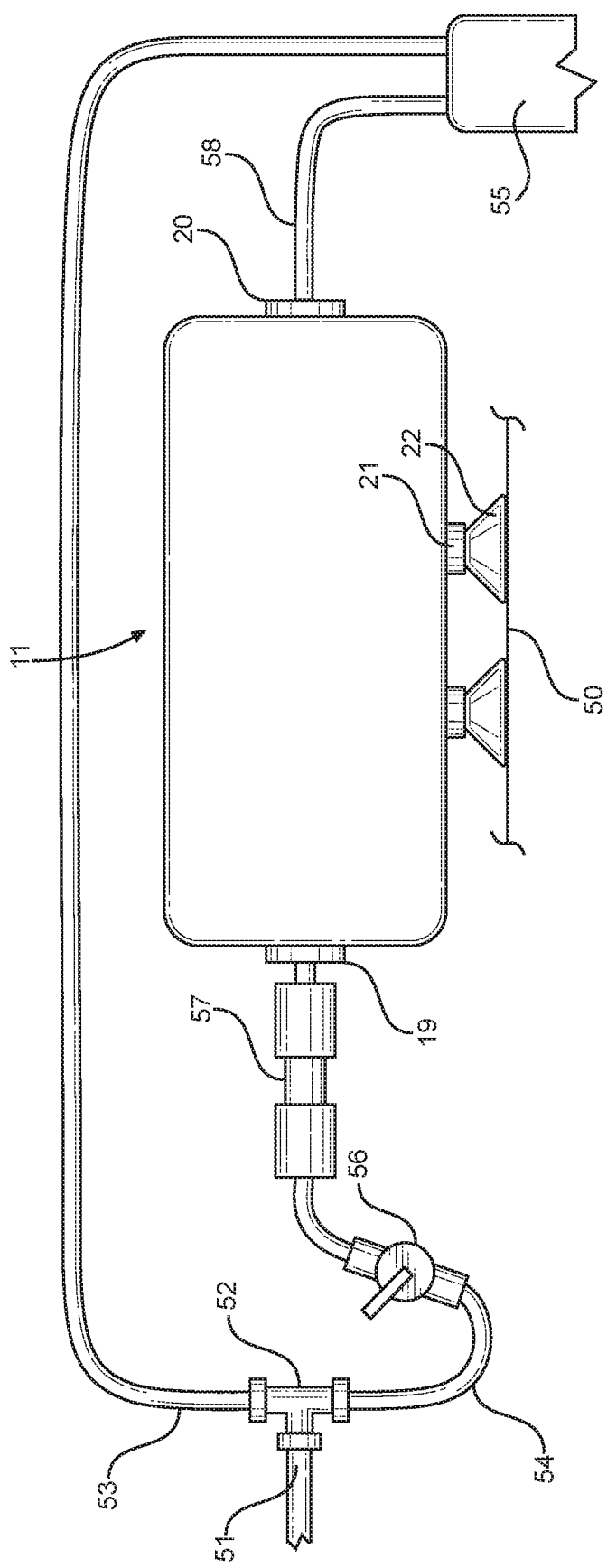
FIG. 5 shows an embodiment of toilet hose connections attached to the chlorine retention reservoir.

Referring to FIGS. 5 and 6, there is shown an embodiment of toilet hose connections attached to the chlorine retention reservoir and an overhead water flow diagram within the interior housing of the chlorine retention reservoir, respectively. The chlorine retention reservoir 11 is configured to be installed within the interior housing of any residential or commercial toilet 50 via fasteners 22. In the illustrated embodiment, the fasteners 22 are suction cups that removably secure within the slots 21 of the reservoir 11. The incoming water line 51 of the toilet is connected to a t-shaped fitting 52 wherein water is diverted to two separate water lines 53, 54. A first line 53 sends water directly to the toilet bowl 55, while the second line 54 sends water to the input port 19 of the chlorine retention reservoir 11.

The second line 54 includes a control valve 56 and a backflow preventer 57 disposed prior to the input port 19. The control valve 56 includes a handle that can adjust the valve 56 to an open and a closed position, wherein the open position allows water to flow through the valve 56 and the closed position prevents water from passing through the valve 56, thus preventing water from entering the chlorine retention device 11. The control valve 56 allows a user to shut off the water flow to the reservoir 11 when a disinfectant chlorine solution is not desired. The control valve 56 allows the end user to increase or decrease the flow of the concentrated chlorine solution. The backflow preventer 57 is configured to prevent any chlorine solution from entering the potable water stream. The backflow preventer 57 also prevents the chlorine solution from contacting and damaging any internal components, such as rubber gaskets, flappers, or the toilet tank housing which may be susceptible to degradation from high concentrations of chlorine.

When the control valve 56 is in the open position, fresh water is sent through the second line 54 and received through the input port 19 of the chlorine retention reservoir 11. Once the water flows through the input port 19, it contacts the first baffle 18A, wherein it is dispersed towards the sidewalls of the housing. Once dispersed the flow of water contacts the second baffle 18B and the third baffle 18C creating turbulence. This turbulence causes the water to contact and mix with the dissolvable chlorine disc 29 stored within the housing, creating a chlorine solution. The planar member of the fourth baffle 18D is configured to contain the solution within the mixing chamber 47 allowing for adequate mixing, while the channel 34 allows the mixture to flow into the discharge chamber 48 where it is discharged through the output port 20. The output port 20 is connected to a discharge line 58 that sends the chlorine mixture directly to the bowl of the toilet. The use of the chlorine retention reservoir 11 prevents the concentrated chlorine mixture from contacting and degrading susceptible internal components of the toilet tank housing, while still effectively disinfecting the toilet bowl.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A chlorine retention reservoir, comprising:
   a housing comprising:
   a base;

a sidewall forming an interior volume having an open upper end;

wherein the open upper end includes a lip extending perpendicularly from the sidewall disposed along a perimeter of the open upper end;

a first baffle affixed to the base, a second baffle and a third baffle affixed to opposing interior sides of the sidewall, and a fourth baffle affixed at a rear portion of the housing;

wherein the first baffle comprises a curved shape, the second baffle and the third baffle comprise a triangular shape, and the fourth baffle comprises a u-shaped panel having two arms extending outwardly from a planar member;

wherein the first, second, third, and fourth baffles are configured to create turbulence that causes water to contact an mix with a dissolvable chlorine disc stored within the housing, creating a chlorine solution;

an input port and an output port disposed on the sidewall of the housing;

a slot disposed on an exterior surface of the housing, wherein the slot is configured to receive a fastener;

a lid having a channel disposed along a perimeter of a lower surface, wherein the channel is configured to receive the lip of the open upper end, such that the lid removably secures to the lip; and a fastener that removably secures to the slot of the housing, wherein the fastener is configured to removably secure to an interior surface of a toilet reservoir.

2. The chlorine retention reservoir of claim 1, wherein the input port is disposed on an upper portion of the sidewall and the output port is disposed on a lower portion of the sidewall.

3. The chlorine retention reservoir of claim 1, wherein the input port and the output port are disposed on opposing sidewalls.

4. The chlorine retention reservoir of claim 1, wherein the slot extends from the base of the housing to a half height of the housing, wherein the height is measured from the base to the lip on the open upper end of the housing.

5. The chlorine retention reservoir of claim 1, wherein the input port and the output port each have a threaded outer surface.

6. The chlorine retention reservoir of claim 1, wherein the fastener is a suction cup.

7. The chlorine retention reservoir of claim 1, wherein a perimeter of the lid extends outwardly past the perimeter of the upper open end of the housing when in an attached position.

8. The chlorine retention reservoir of claim 1, wherein the housing comprises a rectangular shape.

9. The chlorine retention reservoir of claim 8, wherein the housing includes a plurality of curved corners.

10. The chlorine retention reservoir of claim 1, wherein the housing is constructed of a chlorine resistant material.

11. A chlorine retention reservoir, comprising:
a housing comprising:
  a base;
  a sidewall forming an interior volume having an open upper end;
  a lid removably securable over the open upper end;
  a plurality of baffles disposed within the interior volume of the housing, the plurality of baffles comprising a first curved baffle having an apex oriented toward an input port disposed on a first end of the sidewall, a pair of triangular baffles disposed on opposing interior sides of the sidewall, and a planar baffle configured to divide the interior volume into a mixing chamber adjacent the input port and a discharge chamber adjacent an output port on a second end of the sidewall opposing the input port;
a fastener removably secured to a slot disposed on an exterior surface of the housing, wherein the fastener is configured to removably secure to an interior surface of a toilet reservoir.

12. The chlorine retention reservoir of claim 11, further comprising a control valve configured to selectively increase or decrease a flow rate of a concentrated chlorine solution formed within the housing.

13. The chlorine retention reservoir of claim 11, wherein the plurality of baffles are configured to divert and mix water flowing from the input port toward the mixing chamber in order to slowly dissolve a chlorine disc until the saturation point is reached.

14. The chlorine retention reservoir of claim 11, wherein the output port is in fluid communication with a discharge line configured to transport a volume of concentrated chlorine solution directly into a bowl of a toilet to which the housing is secured.

15. The chlorine retention reservoir of claim 11, further comprising a backflow preventer in fluid communication with the input port, wherein the backflow preventer is configured to prevent any chlorine solution from entering a potable water supply stream.

16. The chlorine retention reservoir of claim 14, wherein the backflow preventer is further configured to prevent concentrated chlorine solution from contacting any internal components of a toilet to which the housing is secured.

* * * * *